United States Patent [19]

Sweeney et al.

[11] 4,105,691
[45] Aug. 8, 1978

[54] PROCESS FOR THE PRODUCTION OF CHLOROFLUORINATED CARBOXYLIC ACIDS

[75] Inventors: Richard F. Sweeney, Elma; James O. Peterson, Snyder; Bernard Sukornick, Williamsville; Henry R. Nychka, East Aurora; Richard E. Eibeck, Orchard Park, all of N.Y.; Morris B. Berenbaum, Summit, N.J.

[73] Assignee: Allied Chemical Corporation, Morris Township, Morris County, N.J.

[21] Appl. No.: 642,834

[22] Filed: Dec. 22, 1975

[51] Int. Cl.² ............ C07C 51/24; C07C 51/26
[52] U.S. Cl. ................ 260/530 R; 260/408; 260/514 J; 260/539 A; 260/539 R
[58] Field of Search .......... 260/530 R, 539 R, 539 A, 260/514 J, 408

[56] References Cited

U.S. PATENT DOCUMENTS

| 3,652,640 | 3/1972 | Wadsworth et al. | 260/539 R |
|---|---|---|---|
| 3,661,986 | 5/1972 | Washecheck | 260/530 R |
| 3,752,850 | 8/1973 | Schrerer | 260/539 R |

Primary Examiner—Vivian Garner
Attorney, Agent, or Firm—Jay P. Friedenson

[57] ABSTRACT

Chlorofluorinated carboxylic acids may be effectively produced by an oxychlorofluorination process by reacting a gaseous mixture of a starting material selected from a saturated aliphatic carboxy containing compound, a saturated aliphatic carboxylic acid halide and a saturated aliphatic aldehyde in which all atoms are selected from C, H and O, and corresponding hydrohalogenated compounds in which the halo atoms are selected from chloro and fluoro, or mixtures thereof, an oxygen-containing gas, a chlorinating agent selected from the group consisting of HCl and $Cl_2$ and mixtures thereof, and HF, in the presence of a Deacon catalyst supported by a stable, inert metal salt carrier.

52 Claims, No Drawings

PROCESS FOR THE PRODUCTION OF CHLOROFLUORINATED CARBOXYLIC ACIDS

BACKGROUND OF THE INVENTION

Chlorofluorinated acyclic hydrocarbons are commercially prepared by reacting chlorinated hydrocarbons with hydrogen fluoride in the presence of a fluorination catalyst. In such HF reactions, for each mole of hydrogen fluoride reacted there is one mole of hydrogen chloride liberated. Because by-product hydrogen chloride does not have a steady market even after purification from small amounts of hydrogen fluoride contaminant, it is usually disposed of by dumping in rivers or in the ocean where permitted. The extra cost of this type of disposal is borne by the manufacturing operation. Furthermore, in view of environmental considerations, it is probable that such disposals will be restricted or eventually banned.

Recently, a new process has been developed for the production of chlorofluorinated aliphatic hydrocarbons which comprises reacting a mixture of a hydrocarbon and chlorine and hydrogen fluoride over a fluorination catalyst with a relatively large excess of recycled material consisting of underchlorinated and underfluorinated hydrocarbons. This process, which combines chlorination and fluorination in one step, however, produces more hydrogen chloride per unit weight of chlorofluorinated hydrocarbon than the standard commercial process referred to above. It thus intensifies rather than alleviates the hydrogen chloride by-product problem.

In view of the above discussion, it is apparent that there is a need in the industry for new technology for the manufacture of chlorofluorinated compounds which does not suffer from the hydrogen chloride by-product problem.

The oxychlorination of hydrocarbons by a Deacon type reaction is well known in the art. This involves the chlorination of an alkane or a chloroalkane with chlorine or hydrogen chloride in the presence of an oxygen-containing gas such as air, and in the presence of a Deacon-type catalyst such as a metal halide impregnated on a suitable carrier. It is postulated that in such an oxychlorination reaction, hydrogen chloride is oxidized to chlorine and water and the chlorine thus produced then reacts with the organic material. In this manner, by-product hydrogen chloride is eliminated or at least substantially minimized.

Vapor phase fluorination of chlorinated aliphatic hydrocarbons with and without the presence of a catalyst is also well known.

The combination of an oxychlorination reaction and a fluorination or chlorofluorination reaction into a simultaneous one-step oxychlorofluorination process is suggested in British Pat. No. 745,818, published Mar. 7, 1956. Such a one-step process, if commercially feasible, would be of substantial value not only in the avoidance of the HCl problem but also in the potential savings in capital equipment and energy expenditure.

The British patent is restricted to aliphatic hydrocarbon compounds and, in any event, unfortunately, the process as described is not commercially practical. Attempts to duplicate the catalyst systems described in the British patent have been unsuccessful. The $CuCl_2$ loading recommended in the patent exceeds the absorptive capacity of the carrier by more than two-fold. The excess $CuCl_2$ loading has been found to create serious operating problems such as plugging, corrosion and erratic performance because of undue vaporization and run-off of the $CuCl_2$. Another disadvantage found for such high $CuCl_2$ loading is that it deactivates the fluorination sites on the carrier thus causing a significant decrease in HF conversions.

Others have experimented with fluorination systems for hydrocarbons containing HF, HCl, oxygen and a Deacon type catalyst, but no one to date has reported an effective system capable of supporting an efficient oxychlorofluorination reaction. For example, U.S. Pat. No. 3,476,817, issued Nov. 4, 1969, discloses a chlorofluorination reaction in which an aliphatic hydrocarbon is reacted with chlorine in the presence of HF, a Deacon type catalyst, and oxygen in an amount sufficient to improve the catalyst life. However, the oxygen according to this disclosure is not present in an amount sufficient to accomplish an effective Deacon reaction and accordingly an efficient oxychlorofluorination reaction does not take place. U.S. Pat. No. 2,578,913, issued Dec. 18, 1951, discloses the preparation of fluorinated aliphatic hydrocarbons by reacting a hydrocarbon with HF, in the presence of oxygen, a Deacon-type catalyst and a hydrogen halide promoter, such as HCl. However, the hydrogen halide promoter according to the disclosure is not present in an amount sufficient to accomplish efficient chlorination and accordingly an efficient oxychlorofluorination reaction does not take place. In any event none of the above-mentioned patents teach or suggest reactions of carboxy containing organic compounds or aldehydes.

Accordingly, despite the potential advantages of an oxychlorofluorination process, such a process has not been commercialized. To the best of our knowledge, since publication of British Pat. No. 745,818, no attempts have been reported in the literature to make this a viable process for aliphatic hydrocarbons, much less extend it to other types of compounds, such as carboxy containing compounds, carboxylic acid halides and aldehydes. The reasons for this lack of interest and suspicion of impracticability of the oxychlorofluorination approach are many-fold. As mentioned above, the process as described in British Pat. No. 745,818 cannot be duplicated and cannot be readily adapted for commercially practical results. Further, persons skilled in this art would, in considering commercial feasibility of an oxychlorofluorination process, fear the possibility of explosion and the flammability of hydrogen containing compounds in the oxygen-rich environment present. Also, the likelihood of hydrolysis of the underchlorinated and underfluorinated intermediates is imminent since the reactions occur at relatively high temperatures in the presence of water. Another concern would be the possibility of substantial losses of starting materials, underchlorinated and underfluorinated intermediates and products to combustion. Finally, it would be expected that the system would be unduly corrosive to known materials of construction due to the combined corrosive action of water, HCl and HF at the elevated temperatures required for the reaction.

GENERAL DESCRIPTION OF THE INVENTION

Contrary to the expectations of those skilled in this art, an effective oxychlorofluorination reaction of certain carboxy containing organic compounds, carboxylic acid halides and aldehydes can be achieved, provided that certain critically defined conditions are observed and that a critically defined catalyst system is employed. Contrary to expectation, if such conditions are met, the reaction can be readily controlled without undue danger from explosion and flammability, good yields of products can be obtained without undue loss due to hydrolysis of intermediates or combustion reactions and, quite surprisingly, known materials of construction can be used for the apparatus with tolerable corrosion rates.

This may be accomplished by reacting a gaseous mixture of a starting material selected from a saturated, aliphatic, carboxy

containing compound, a saturated, aliphatic, carboxylic acid halide and a saturated aliphatic aldehyde in which all atoms are selected from C, H and O, and corresponding hydrohalogenated compounds in which the halo atoms are selected from chloro and fluoro, or mixtures thereof, oxygen in an oxygen-containing gas, HCl or Cl$_2$ and HF, in the presence of a Deacon catalyst supported by a stable inert metal salt carrier, with the weight percentage of cation in the Deacon catalyst ranging from about 0.6–20 based on the total cation content of the Deacon catalyst and metal salt carrier, at elevated temperatures and with a contact time of from about 0.1 to 20 seconds. Successful results depend on the combination of use of the Deacon catalyst, with the cation content in the indicated weight percent range, and use of the relatively short contact times specified. The preferred carboxy containing compounds are selected from carboxylic acids, carboxylic acid halides and carboxylic acid anhydrides.

The major products of these reactions are chlorofluorinated carboxylic acids regardless of the choice of starting material within the scope of the invention. In addition to the oxychlorofluorination reaction, the presence of oxygen causes the oxidation of aldehydes to carboxylic acids. Water formed by the oxidation of HCl hydrolyzes the anhydrides and carboxylic acid halides to the corresponding carboxylic acids.

The chlorofluorinated carboxylic acid products are a well-known class of compounds and are useful as surface active agents particularly as their alkali metal salts. The highly fluorinated carboxylic acids produced according to the invention possess particularly high surface activity and may be used as anti-wetting agents and as emulsifying agents in conventional manner. Lower fluorinated materials can be converted to higher fluorinated material by auxilliary fluorinating techniques. Such highly fluorinated and/or chlorofluorinated carboxylic acids may be converted to the corresponding carboxylic acid chlorides, by conventional techniques which have utility as solvents and sealing adjuvants for films of polymers, terpolymers and copolymers of trifluorochloroethylene. The chlorofluorinated carboxylic acids produced according to the invention may be polymerized such as with vinyl compounds, e.g. vinyl acetate, by conventional techniques, to produce polymeric compositions useful as non-flammable coatings.

DETAILED DESCRIPTION OF THE INVENTION

It is theorized that in the oxychlorofluorination reaction, chlorination, oxidation and fluorination reactions all take place simultaneously. The chlorination reaction replaces one or more available hydrogen atoms in the starting material with chlorine to give a chlorinated product and HCl. In the presence of a suitable Deacon catalyst, as will be described in more detail hereafter, the HCl is oxidized back to chlorine which then is available for further chlorination. Oxidation of any aldehydes, also takes place, as indicated above. Water is formed and hydrolyzes any anhydrides or acid halides to the corresponding carboxylic acids. In the presence of a fluorination catalyst, or under suitable thermal conditions, the chlorinated products are fluorinated by HF to yield fluorinated products. It is not feasible to produce very highly fluorinated products in the oxychlorofluorination environment, except in the case of lower molecular weight products, particularly those containing two carbon atoms, where due to the activating influence of adjacent carboxyl or aldehyde groups, the remaining carbon atom can be perchlorinated and then perfluorinated. Depending on the conditions chosen, the final products are more or less partially fluorinated and may or may not contain hydrogen.

The expression "saturated, aliphatic, carboxy containing compounds in which all atoms are selected from C, H and O," refers to compounds of the class indicated which contain only C, H and O atoms. These starting materials of this invention are known classes of compounds and are either commercially available or may be prepared by conventional methods.

The starting materials should be capable of vaporization without extensive decomposition under the Deacon oxidation conditions (300°–600° C.). For this reason, generally, the starting materials preferably contain from 2 to 18 carbon atoms. The starting materials in the upper part of this range are solids and must be melted and pumped in liquid phase to a preheater vaporizer where mixing with other components of the gas feed stream is effected. Preferably, the starting materials contain from 2–6 carbon atoms.

The halogen atoms of the carboxylic acid halide starting materials are preferably chlorine or fluorine.

Illustrative suitable starting materials according to the invention include acetic acid, n-butyric acid, isobutyric acid, 2-methylpropanoic acid, dimethylacetic acid, caproic acid, capric acid, lauric acid, myristic acid, palmitic acid, stearic acid, cyclohexane carboxylic acid, acetyl chloride, n-butyryl fluoride, isobutyryl iodide, 2-methylpropionyl chloride, dimethylacetyl chloride, caproyl bromide, caproyl chloride, n-lauryl chloride, n-myristyl fluoride, n-palmityl fluoride, n-stearyl chloride, cyclohexanoyl chloride, acetic anhydride, n-butyric anhydride, isobutyric anhydride, 2-methyl propionic anhydride, dimethylacetic anhydride, caproic anhydride, n-lauric anhydride, n-myristic anhydride, n-palmitic anhydride, n-stearic anhydride, cyclohexane carboxylic anhydride, acetaldehyde, n-butyraldehyde, isobutyraldehyde, 2-methyl propionaldehyde, dimethylacetaldehyde, caproaldehyde, n-lauraldehyde, n-myristaldehyde n-palmitaldehyde, n-stearaldehyde and cyclohexanal.

The corresponding hydrohalogenated class of starting materials are those starting materials described above in which one or more of the hydrogen atoms are replaced with halo atoms selected from fluorine and chlorine. These materials must contain at least one hydrogen atom. The halo atoms may be all chloro, all fluoro, or both. Preferably, these starting materials contain more atoms of hydrogen than halogen. Still preferably, the number of fluorine atoms in the molecules does not exceed more than one for each carbon atom present.

Illustrative suitable starting materials of this class adre monochloroacetic acid, 3-chloro-4-fluorooctadecanoic acid, monochloroacetyl chloride, 3-chloro-4-fluorooctadecanoyl fluroide, monochloroacetic anhydride, 3-chloro-4-fluorooctadecanoic anhydride, monochloroacetaldehyde and 3-chloro-4-fluorooctadecanal.

The "oxygen-containing gas" refers to oxygen or an oxygen-containing mixture with gases which are not reactive under the process conditions employed. Examples of suitable oxygen-containing gas mixtures include oxygen enriched air, air mixed with inert gases and mixtures of oxygen, air and inhert gases. The theoretical quantity of oxygen in an oxygen-containing gas required for the oxychlorination reaction is the stoichiometric amount required to convert C—H bonds to C—Cl bonds in accordance with the following formula:

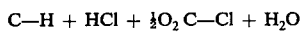

In other words, 0.50 mole oxygen for each C—H bond in the starting material desired to be reacted is stoichiometrically required. An 80% deficiency may be employed with satisfactory results, or at least 0.10 mole oxygen for each C—H bond in the starting material. Depending on the nature of the starting materials and final products desired, it may be preferred to employ at least 0.25, preferably at least 0.50 mole, and, still preferably, up to about a 50% excess, or 0.75 mole oxygen, or more, for each C—H bond in the starting material. As noted above, in the case of aldehyde starting materials which are oxidized during the course of the reaction, some oxygen is, of course, utilized for this reaction. Compensation may have to be made to stoichiometrically favor all the described oxidation reactions. Large excesses of oxygen will not deleteriously affect the reaction except for the possibility of creating a flammability problem.

HCl or chlorine may be used as the chlorine source for the oxychlorofluorination reaction. If HCl is used, it may be supplied from an outside source or, it may be prepared in situ, by the reaction of the HF feed with a chlorine-containing hydrohalogenated starting material if present.

The theoretical quantity of HCl or $Cl_2$ used in the reaction is the stoichiometric amount required for the desired hydrogen replacement in the starting material. This amounts to 1 mole of HCl or equivalent of $Cl_2$ (0.5 mole) for each C—H bond desired to be reacted in the starting material. A 90% deficiency of HCl or equivalent of $Cl_2$, or 0.10 mole HCl or equivalent of $Cl_2$, for each C—H bond present in the starting material, may be employed with good results, particularly if it is desired to favor the production of lower chlorinated products. Depending on the nature of the final product desired, it may be preferred to employ at least 0.25, preferably at least 0.50, and still preferably, at least 0.75 mole HCl or equivalent of $Cl_2$ for each C—H bond present in the starting material. Excess HCl or $Cl_2$ may be used to insure maximum conversions to the highly chlorinated products without deleterious effects. If it is desired to preserve some C—H bonds in the final product, a somewhat greater deficiency of HCl or chlorine should be employed, but in no event less than 2.0 moles of HCl or equivalent of $Cl_2$ for each mole of starting material.

In the case that HCl is charged, such would be converted to chlorine by the Deacon reaction and chlorine would then be the active chlorinating agent.

The quantity of HF to be employed is equal to at least one mole of hydrogen fluoride per mole of starting material for every fluorine atom desired in the end product which is to be achieved by the fluorination reaction. The oxychlorofluorination environment does not favor the formation of very highly fluorinated products. It is not generally feasible to obtain substantially greater than 1.0-1.4 fluorine atoms per each carbon atom in the product. Large excesses of hydrogen fluoride may be used, however, without adversely affecting the reaction and may in fact be advantageous in assisting in control over reaction temperatures.

The Deacon catalysts are the oxychlorination or Deacon-type reaction catalysts which are well known in the art. The most active catalysts of this type are the oxides and halides of multivalent metals having variable valence states. Illustrative of such metals are Cu, Sn, Ni, Rh, Fe, V, Mn, Co, Pd, Cd, Hg, Pb, Ce, and Cr. The preferred metal is Cu. The preferred forms of these metals are the halides, especially the chlorides. Illustrative suitable Deacon catalysts are $CuCl_2$, $Cu_2O$, $CuO$, $FeCl_2$, $FeCl_3$, $FeO$, $Fe_2O_3$, $Cu_2Cl_2$, $Cr_2O_3$, $CrCl_3$, $MnCl_2$, $MnBr_2$, $MnO_2$, $SnCl_2$, $NiBr_2$, $RhCl_3$, $VCl_3$, $CoO_2$, $PdCl_2$, $Cd(NO_3)_2$, $HgBr_2$, $PbCl_2$ and $Ce(NO_3)_3$. The preferred Deacon catalyst is copper chloride. Mixtures of Deacon catalyst may be employed. Other metal salts such as alkali or alkaline earth metal chlorides may be combined with the Deacon catalyst. These may serve to promote the Deacon reaction, promote the fluorination and chlorination reactions or inhibit combustion and undesirable hydrolysis reactions, that is to say other than the readily hydrolyzable sulfonyl halide groups. Illustrative suitable metal salts of this type are the chlorides of Li, Na, K, Rb, La, Th, Ce, Ta, and Cs. In order to achieve a significant amount of promotion, it is desirable to use at least .5 mole of the metal salt promoter per mole of Deacon catalyst. Large excesses of the metal salt promoter will not deleteriously affect the reaction. Generally, it is preferable to employ from about 1-2 moles of salt promoter per mole of Deacon catalyst and, still preferably, about 1 mole of metal salt promoter per mole of Deacon catalyst.

The Deacon catalyst is used in combination with a stable, inert metal salt carrier.

By "stable" is intended to mean that the carrier is dimensionally and physically stable in the sense that when used in a fixed bed reactor, no more than 20% by weight of the carrier crumbles or converts to a power from its original granular or pelleted form after 500 hours of operation, or when used in a fluidized bed reactor, the carrier does not undergo erosion or agglomeration to the extent that the particle size distribution changes sufficiently to adversely affect the operation of the fluidized bed. Acceptable particle size distributions for fluidized bed reactions are set by standard engineering practice well known to persons skilled in the art. It is also a characteristic of being "stable" for the purpose of this description that the carrier is substantially non-volatile and non-melting at temperatures up to about 550° C.

By "inert" is intended to mean that which is or becomes substantially non-reactive with the organic starting materials, HF, HCl if used or prepared in situ, $Cl_2$ and $O_2$. Some minor reaction with the aforementioned materials can be tolerated provided that such reaction does not adversely affect the oxychlorofluorination reaction or the catalyst life. Alumina ($Al_2O_3$) is not considered to be inert within this definition because it undergoes substantial reaction with HF under oxychlorofluorination conditions. An example of a permissible minor reaction is the formation of small amounts of fluorides and/or oxyfluorides which will not further react with the aforementioned materials. The term "inert" is not intended to exclude catalytically active materials provided such materials satisfy the other requirements for being inert as described above. For example, a material satisfying the requirements for the stable, inert, metal salt carrier as defined herein, may also function as a fluorination or Deacon catalyst, as defined herein. In the latter event, for the purposes herein, the expression Deacon catalyst supported by a stable, inert metal salt carrier can refer to a single substance. A preferred embodiment of the stable inert meta salt carrier are those carriers which are fluorination catalysts, such as $AlF_3$.

A variety of metal salts meet these criteria of being stable and inert including, for example, chlorides, fluorides, oxyhalides, or oxides and admixtures thereof of Al, Mg, Ca, Ba, V, Th, Sr, Co, Ni, Cd, Pb, Cr and Fe, or combinations thereof. Illustrative suitable metal salts are $AlF_3$, $MgF_2$, $CaF_2$, $BaF_2$, $V_2O_3$, $ThF_4$, $SrF_2$, $CoF_2$, $NiF_2$, $CdF_2$, PbO, $CrF_3$ and $Fe_2O_3$. The preferred anion for the meta salt carriers is fluoride. The preferred cation is aluminum and the preferred support material is $AlF_3$. Depending on the results desired, choice of the stable, inert metal salt support may have a substantial influence on the particular oxychlorofluorination reaction involved. As indicated above, the support may catalyze the fluorination reaction. It may also influence the degree of Deacon reaction obtained, the degree to which the HF reactant is utilized and the loss of the starting materials to combustion and undesirable hydrolysis.

The metal salt used as the support may be prepared beforehand or formed in situ during the reaction. For example, the Deacon catalyst may be impregnated on alumina (aluminum oxide). Under oxychlorofluorination conditions, particularly exposure to HF at elevated temperatures, the surface of the alumina is converted to $AlF_3$. The process aspects of this invention employing such catalysts are considered to be part of the invention herein, although this is not a preferred mode of operation. Preferably, the support throughout the oxychlorofluorination reaction comprises at least about 80% by weight of the metal salt and, still preferably, at least about 90% by weight of the metal salt. German Pat. No. 2,114,457 discloses a number of chlorofluorination catalysts including $CuCl_2$ impregnated on a support such as aluminum oxide in which the catalyst loading is between about 1-10 weight percent metal based on the total weight of the catalyst salts and the support material. It is disclosed that during the chlorofluorination reaction the surface of the aluminum oxide is presumed to be converted to $AlF_3$; however, it is not believed possible to achieve at least 80% weight percent $AlF_3$ in this manner, principally since the normal chlorofluorination reaction temperatures are not high enough for optimum conversions of aluminum oxide to $AlF_3$.

The preferred support material, $AlF_3$, may be prepared by fluorinating alumina with HF at elevated temperatures. The alumina starting material for the supports is commercially available. Either the commercially available alpha or gamma aluminas may be employed; however, it has been found that a superior carrier is formed by fluorination of gamma alumina. The aluminas may be readily fluorinated in their commercially avialable form as granules or pellets with anhydrous HF diluted with nitrogen at temperatures ranging from about 200°–650° C. It is preferred to conduct a substantial portion of the fluorination at the upper portion of this range, preferably at about 500°–650° C. Most preferred, in fact, is to maintain the temperature at about 650° C. for the entire fluorination. At low fluorination temperatures a mixture of alpha and gamma forms of $AlF_3$ is obtained. At high fluorination temperatures the alpha form of $AlF_3$ is obtained. It has been found that the alpha form of $AlF_3$ is superior to the gamma form for oxychlorofluorination purposes. The gamma form of $AlF_3$ may also be prepared by the fluorination of $AlCl_3$ or the thermal decomposition of $(NH_4)_3AlF_6$. The alpha form may also be readily prepared by reacting $Al(OH)_3$ with HF.

It is essential according to the invention process that the weight precentage of cation in the Deacon catalyst during the oxychlorofluorination reaction be in the range of 0.6–20, preferably 1–16 and, still preferably, 2–8, based on the total cation content of the Deacon catalyst and the stable, inert metal salt carrier. For the purpose of determining the weight percentage of cation in the Deacon catalyst, the presence of cations in any additional metal salt promoters which are not themselves Deacon catalysts, shall be ignored. It is within the scope of this invention to charge a supported Deacon catalyst to the oxychlorofluorination reaction in which the cation content of the Deacon catalyst exceeds the maximum 20 weight percent level defined herein and subsequently during the course of the oxychlorofluorination reaction to permit the Deacon catalyst cation content to fall to within the claimed limits. Use of a concentration of Deacon catalyst substantially in excess of the above-described 20 weight percent limitation on cation concentration, however, results in an unstable catalyst with low activity and which creates corrosion problems. Such catalysts cannot be fluidized if desired and cannot be reused.

For example, in the oxychlorofluorination reaction disclosed in British Patent 745,818, it is disclosed that 31 weight percent $CuCl_2$ be impregnated into $AlF_3$/NaCl. On the basis of cation content of the Deacon catalyst based on the total cation content of the Deacon catalyst and the support, this amounts to 38.6 weight percent. Attempts to duplicate this catalyst have failed. It has been found that such 31 weight percent $CuCl_2$ loading exceeds the absorptive capacity of the carrier by more than two-fold. Only 23 weight percent $CuCl_2$ was able to be impregnated. When this 23 weight percent $CuCl_2$ was tested in an oxychlorofluorination reaction, there was considerable run-off of $CuCl_2$ so that only about 15 weight percent $CuCl_2$ loading was actually achieved. This run-off and the vaporization of the excess $CuCl_2$ caused severe operating problems, such as plugging and erratic performance. The excess $CuCl_2$ also created a corrosion problem with the metallic reactor walls. A low catalytic activity was also noted with this catalyst and this was attributed to be caused by the deactivation of fluorination sites on the carrier by the excess $CuCl_2$, thus decreasing HF conversions.

Any conventional technique may be employed for placing the catalyst material on the metal salt carrier. The object is to accomplish the most uniform distribution of catalytic material on the carrier as is possible. By way of illustration the catalytic material may be sprayed upon the support particles in mixing devices, a solution containing the catalyst may be sprayed into a fluidized bed of the carrier particles, or the carrier particles may be simply immersed in a solution containing the catalyst material followed by evaporation of the solution.

Reaction temperatures are elevated and may vary depending on the starting material chosen, the catalyst and other factors. Generally, reaction temperatures should be maintained between about 300°–600° C., preferably between about 350°–450° C. If the reaction temperature is excessive in a particular environment, then the combustion or undesirable hydrolysis of the starting materials may become excessive. If the reaction temperature is unduly low, there will be a decline in the chlorination and fluorination reactions. The ideal reaction temperature for a particular oxychlorofluorination environment will depend on the starting materials chosen, the catalyst and other factors, as can readily be determined by those skilled in the art assisted by the considerations discussed above.

Contact time is critical. Contrary to the disclosure of British Pat. No. 745,818 which suggests a contact time of approximately 24 seconds, it is essential not to employ a contact time over about 20 seconds. If contact times substantially above 20 seconds are employed, substantial losses to combustion and to undesirable hydrolysis occur and the production capacity per unit volume of catalyst decreases. For example, with the preferred catalyst system of $CuCl_2$ on $AlF_3$, at approximately 24 seconds contact time, production of $CO_2$ is 4–5 times greater than at a contact time of approximately 2–6 seconds. If the contact times are too low, satisfactory conversion rates cannot be obtained. Accordingly, contact times must be maintained between about .1 to 20 seconds, preferably between about 2–12 seconds. For fixed bed operation, the preferred contact time is from about 1–18 seconds and, still preferably, from about 2–6 seconds. For dynamic or fluidized bed operation, the preferred contact time is between about 3–20 seconds and, still preferably, from about 6–12 seconds. By "contact" time (C.T.) is intended to mean essentially the residence time that the feed materials contact each other in the presence of the catalyst, or, more precisely in the case of a fixed bed design (X):

$$C.T. X \text{ (seconds)} = \frac{\text{Catalyst Volume (ml)} \times 273° K \times 3600/\text{sec/hr} \times \text{pressure (atm)}}{22,400 \text{ ml} \times \text{reactor temperature (° K)} \times \text{moles (reactants)/hr.}}$$

In the case of a fluid bed design (L):

$$C.T.L. \text{ (seconds)} = \frac{\text{Bed Height (ft.)}}{\text{Superficial Gas Velocity (ft./sec)}^*}$$

$$* \frac{\text{Volume of gas/sec. (ft.}^3/\text{sec)}}{\text{cross-sectional area (ft.}^2) \text{ of reactor}}$$

Pressure is not a critical consideration as the reactions described herein may be conducted under atmospheric pressure or superatmospheric pressures. In the preferred embodiment, superatmospheric pressures are employed, preferably up to about 200 p.s.i.g. and, still preferably, from about 20–75 p.s.i.g.

The chlorination, fluorination and Deacon reactions are highly exothermic. It is desirable to control the exothermic heat of such reaction to avoid pyrolysis, carbonization, combustion and other undesirable side reactions.

Mechanical cooling means may be employed to control the exotherm, such as cooling jackets, cooling spray, cooling coils or other suitable heat exchange means. Another way to control the exotherm is by diluting the catalyst with an inert, solid material such as fused alumina.

Another way to control the exotherm is by adding an inert gas to the reaction gas stream. By "inert gas" is intended to mean an organic or inorganic gas which is inert to reaction with the organic reactants and with chlorine, oxygen, water or HCl, but not necessarily inert to reaction with hydrogen fluoride. Illustrative suitable inert inorganic gas diluents are nitrogen, hydrogen chloride, helium and argon. Illustrative suitable inert organic gas diluents are carbon tetrafluoride, hexafluoroethane and carbon tetrachloride.

The amount of diluent to be used is that which is needed to control the reaction temperature of the particular reaction involved. This will depend on the amount of chlorination taking place and the nature of the diluent used. The preferred amount of diluent may be readily determined by those skilled in the art. Generally, the molar ratio of the diluent to the carbon containing feed materials ranges from about .5–4:1, with the preferred ratio ranging from about 1–2:1. At the end of the reaction, the diluent may either be recycled or discarded.

Any combination of the above-described means of temperature control may be employed.

The process of the invention is carried out by passing the gaseous reactants through a bed of the supported catalyst material in finely divided or granular solid form. The catalyst bed may be operated as a fixed bed, that is to say by keeping the gas velocity low enough that the bed of solid catalyst particles remains essentially static. The catalyst bed may also be operated as a dynamic bed. By increasing the gas velocity of the reactants some of the catalyst particles become dynamically suspended in the reactant gas stream. The height of the catalyst bed therefore expands. Such beds are generally referred to as "dynamic beds". As is known in the art, if the gas velocity is increased still further, all the catalyst bed particles become suspended and ultimately the bed may assume a highly turbulent condition known and referred to as a fluidized bed. Exact conditions required to establish a fluidized bed condition depend on the particle size of the catalyst components, the gas velocity, the density of the particles and other factors. A discussion of such factors as are necessary for establishing and maintaining a fluidized bed may be found in Wilhelm Kawak *Chemical Engineering Progress*, Vol. 44, Page 201 (1948).

Preferably the process of the invention is carried out in a continuous manner using a reactor comprising a plurality of vertical tubes which are charged with the supported catalytic material is finely divided or granular form. Preferably the catalyst is maintained in a fluidized state. The starting material, the oxygen-containing gas, the chlorinating agent and hydrogen fluoride are metered into the bottom of the reactor tubes through the calibrated flowmeters. Prior to entry into the bottom of the reactor tubes the reactants are preheated to approximately the reaction temperature desired. Separate feed lines should be used for materials which would otherwise prematurely react before passage to the reactor tubes. For example, many of the starting materials and chlorine will react thermally if present in the same heated lines. Accordingly, these materials should be fed through separate lines. In accordance with the description herein, optional additional feed streams may be fed into the bottom of the reactor, such as an inert diluent stream. Liquid reactants may be metered from calibrated reservoirs through pumps.

At the inlets to the fixed catalyst bed, relatively short hot zones will develop. These zones are generally 50°–100° C. higher in temperature than the reactor temperatures. Such temperature gradients are tolerable however. If excessive temperatures are generated in the hot zones, undesirable combustion and carbonization reactions could result. In such an event, the temperatures of such hot zones should be controlled by employing any of the methods discussed herein for exotherm control.

Pressures, temperatures, contact times and flow rates of reactants are regulated to produce the desired product composition with optimum yields and utilizations of reactants in accordance with the discussion herein. Reaction products are continuously removed from the top of the reactor tubes.

Recovery and purification of the desired products, by-products and unreacted reactants, may be accomplished by conventional means such as distillation. Catalyst particles carried over in the exiting product gases may be separated by cyclones for return to the reactor. The product gases may then be cooled and partially condensed. Condensed aqueous HCl and HF are phase-separated from condensed organics, and may be recycled to the reactor after partial or complete dehydration. Condensed organics may be revaporized for further purification, or treated as a liquid phase. Organic vapors are neutralized by contacting with dilute caustic in a scrubber. The organic vapors may then be dried by contacting with concentrated sulfuric acid. The dried neutralized organic vapors are then compressed and fed to a distillation unit (still) to separate low boiling components, such as $CO_2$, oxygen and other trace low boilers, from higher boiling components. A series of continuous distillations is used to separate the higher boiling materials into discrete products. The products may be further purified, if desired, by contacting with molecular sieves.

A variety of modifications and variations of product recovery and purification may be employed by persons skilled in the art and will depend on the nature of the feed materials and product mixes obtained. Such procedures are well within the skill of the art and do not form a part of this invention.

Materials of construction for the reactor and associated equipment should be resistant to the reactants in the environment employed. In general, metals such as Inconel and Hastelloy are sufficiently resistant to corrosion in the presence of the reactants of the oxychlorofluorination process. The corrosion rate is lower in fluidized bed operations than in fixed bed operations. For this reason alone, fluid bed operation is preferred. In both fluid bed operation and fixed bed operation liners of fused high purity alumina (99.8%) perform well in terms of exhibiting low corrosion rates, withstanding high temperature exposure and providing good heat transfer through the reactor walls. Sintered Inconel 600 has proved of particular value as a construction material for the distributor bed supports in the fluid bed reactor.

The following examples illustrate practice of the preferred embodiments of the invention and attempts to practice the invention described in British Pat. No. 745,818. The advantages of the present invention will be apparent therefrom. In the examples, the stated reactant feed rates were measured at 25° C./atmospheric pressure, temperatures refer to degrees Centigrade, and the following terms, unless otherwise specified, have the meanings given below.

$$\% \text{ HF Conversion (moles)} = \frac{\text{HF consumed}}{\text{HF in}} \times 100$$

$$\% \text{ starting material Conversion (moles)} = \frac{\text{starting material in} - \text{starting material out}}{\text{starting material in}} \times 100$$

$$\% \text{ Cl}_2 \text{ Conversion (mols)} = \frac{\text{Cl}_2 \text{ in} - \text{Cl}_2 \text{ out} \times 100}{\text{Cl}_2 \text{ in}}$$

$$\% \text{ HCl Utilization* (moles)} = \frac{\text{HCl in} + \text{HF consumed} - \text{Cl out}}{\text{HCl in} + \text{HF consumed}} \times 100$$

*If $Cl_2$ is in feed, then substitute $Cl_2$ in for HCl in.
ml = Milliliters
g = Grams
m²/g = Square Meters/Gram
cc/g = Cubic Centimeters/Gram
l/h = Liters/Hour
I.D. = Internal Diameter
m/h = Moles/Hour

EXAMPLE 1

This example demonstrates a typical preparation of $AlF_3$, the preferred carrier material:

A 834 g. sample of ⅛ inch diameter alumina pellets (Harshaw Al-1404), having a surface area of 190 m²/g and a pore volume of 0.46 cc/g, was charged to a 2 inch I.D. × 22 inches long Inconel tubular reactor to form a bed. The reactor was immersed in a fluidized sand bath the temperature of which was controlled at 550° ± 5°. During the heating up period, 25 g. of water were evolved under a small nitrogen sweep of 5 l/h. A steam of HF varying between 50-57 g/h and diluted with $N_2$ was then introduced. A "hot spot" temperature ranging from 644° to 662° immediately developed and gradually migrated from the inlet end of the bed to the outlet end. The signs of the completion of fluorination were: (1) HF was no longer being absorbed as measured by comparing HF input against HF output and (2) the "hot spot" temperature decreased to the level of the sand bath temperature of 550°. After 20 hours the fluorination was complete but HF introduction was continued for 3 hours remote. The $AlF_3$ content in the resulting catalyst pellets was 90%. The catalyst had a pore volume of .13 cc/g and a surface area of 3.4 m²/g. X-ray diffraction pattern indicated the alpha form of $AlF_3$.

EXAMPLE 2

This example demonstrates impregnation of the $AlF_3$ carrier material prepared according to Example 1, with the preferred Deacon catalyst, $CuCl_2$. The catalyst was promoted with KCl.

125 ml of an aqueous solution of $CuCl_2 \cdot 2H_2O$ (16.0 g.) and KCl (7.0 g.) were added to the $AlF_3$ prepared according to Example 1, which was contained in a flask under vacuum. The flask contents were shaken slightly to insure a uniform coating of the pellets. After drying overnight at 100° in vacuo, the $AlF_3$ contained 2.0% $CuCl_2$ and 1.1% KCl or, on a metal basis, 95.3% Al, 2.9% Cu and 1.8% K.

EXAMPLES 3-10

These examples show a typical oxychlorofluorination procedure carried out according to the invention:

A 450 ml or 559 g. sample of the supported catalyst prepared according to Example 2 and preconditioned by heating at 450° for 2 hours with HF at a flow rate of 40 g/h is charged into a 1½ inch I.D. × 24 inch long Inconel pipe reactor to a depth of 14 inches. The reactor is immersed into a temperature controlled sand bath at 400° C. With the sand bath temperature at 400°, flow of the starting materials, $Cl_2$ and HF, at the rates indicated below, is started through the reactor. Fifteen minutes later flow of $O_2$ is started. To obtain a ten second contact time for a 450 ml. sample of catalyst at 400°, the flow rates indicated below are used with the corresponding molar ratios shown.

TABLE I

| Examples | Starting Material | | Flow Rate (moles/hr.) | Molar Ratio |
|---|---|---|---|---|
| 3 | acetic acid | | 0.44 | 1 |
| | | $Cl_2$ | 0.55 | 1.25 |
| | | HF | 1.32 | 3.0 |
| | | $O_2$ | 0.56 | 1.25 |
| 4 | n-stearic acid | | 0.14 | 1.0 |
| | | $Cl_2$ | 0.72 | 5.0 |
| | | HF | 1.44 | 10.0 |
| | | $O_2$ | 0.57 | 4.0 |
| 5 | acetyl chloride | | 0.22 | 1.0 |
| | | $Cl_2$ | 0.44 | 2.0 |
| | | HF | 1.55 | 3.0 |
| | | $O_2$ | 0.66 | 3.0 |
| 6 | n-stearyl fluoride | | 0.14 | 1.0 |
| | | $Cl_2$ | 0.72 | 5.0 |
| | | HF | 1.44 | 10.0 |
| | | $O_2$ | 0.57 | 4.0 |
| 7 | acetic anhydride | | 0.24 | 1 |
| | | $Cl_2$ | 0.60 | 2.50 |
| | | HF | 1.43 | 6.0 |
| | | $O_2$ | 0.60 | 2.50 |
| 8 | n-stearic anhydride | | 0.14 | 1.0 |
| | | $Cl_2$ | 0.72 | 5.0 |
| | | HF | 1.44 | 10.0 |
| | | $O_2$ | 0.57 | 4.0 |
| 9 | acetaldehyde | | 0.44 | 1 |
| | | $Cl_2$ | 0.55 | 1.25 |
| | | HF | 1.32 | 3.0 |
| | | $O_2$ | 0.56 | 1.25 |
| 10 | stearaldehyde | | 0.14 | 1.0 |
| | | $Cl_2$ | 0.72 | 5.0 |
| | | HF | 1.44 | 10.0 |
| | | $O_2$ | 0.57 | 4.0 |

All gas flows are measured by calibrated flowmeters. HF flow is measured by a differential pressure cell and the liquid flow is measured with a calibrated pump. After about one hour the temperature profile of the catalyst stabilizes. The reactions are conducted over a 4 hour period under the above specified conditions during which time effluent samples were taken at various intervals for analysis. Analysis for the organic components is achieved by a gas chromatograph which is connected to a mass spectrograph. The acidic components, HF, HCl, $Cl_2$ and $CO_2$ are determined by passing the samples through a caustic solution and analyzing by standard methods. The analyses show appreciable formation of chloro and chlorofluoro-substituted carboxylic acid products and aldehyde products.

In all of Examples 3–10 the expected conversions for HF and $Cl_2$ are obtained as well as a significant extent of the Deacon reaction. This demonstrates that an oxychlorofluorination reaction take place.

EXAMPLES 11–20

Examples 11–18 were conducted identically to Examples 3–10 and Examples 19–20 were conducted identically to Examples 9–10 except that the catalyst compositions vary as indicated in the following Table. Oxychlorofluorination proceeds in all the examples with satisfactory levels of HF, $Cl_2$ and starting material conversions and Deacon reactions.

TABLE II

| Example | % Al | Cu | K | Other Metals | Cation Content of Deacon Catalyst** |
|---|---|---|---|---|---|
| 11 | 95.3 | 2.9 | 1.8 | | 3.0 |
| 12 | 74.3 | 16.0 | 9.7 | | 17.8 |
| 13 | 99.1 | .60 | .34 | | .60 |
| 14 | 78.2 | 8.0 | 4.9 | La 8.9 | 9.3 |
| 15 | 86.3 | 2.8 | 1.7 | La 9.2 | 3.1 |
| 16 | 94.3 | 2.9 | 1.8 | Fe* 1.0 | 4.0 |
| 17 | 85.4 | 2.7 | 1.7 | Th 10.2 | 3.1 |
| 18 | 84.2 | 8.6 | 2.7 | La 3.0 Ce 1.5 | 9.2 |
| 19 | 91.3 | 2.8 | — | Cs 5.9 | 3.0 |
| 20 | 67.5 | 13.3 | — | Ta 19.2 | 16.5 |

*Additional Deacon Catalyst
**Based on total cation content of the Deacon Catalyst and metal salt carrier, excluding promoters.

EXAMPLES 21–24

These Examples demonstrate an oxychlorofluorination reaction in which the chlorine is generated in situ by the reaction of HF with a chlorine-containing hydrohalogenated starting material. A 620 ml (629 g.) sample of granular $Cr_2O_3$ was impregnated with 7.8% $CuCl_2$/3.5% KCl to give a catalyst having a metal composition of 90.6% Cr, 6.3% Cu and 3.1% K (Deacon cation concentration — 6.5%). An HF stream at the rate of 50 g/h was passed through the impregnated material for eight hours at a temperature from 340° to 410° to form $CrF_3$. On the basis of weight gain, the $CrF_3$ content of the catalyst was about 42%.

Gaseous mixture of various hydrohalogenated starting materials, HF and $O_2$ are passed through the thus prepared $CrF_3$ catalyst at 400° and with a contact time of about 13.6 seconds. After about 1 hour, gas chromatographic analyses of the effluents were conducted. The starting materials and flow rates employed are shown in the following table:

TABLE III

| Example | Starting Materials | Flow Rate (moles/hr) |
|---|---|---|
| 21 | monochloroacetic acid | 0.44 |
| | HF | 1.32 |
| | $O_2$ | 0.56 |
| 22 | monochloroacetyl chloride | 0.44 |
| | HF | 1.32 |
| | $O_2$ | 0.56 |
| 23 | monochloroacetic anhydride | 0.44 |
| | HF | 1.32 |
| | $O_2$ | 0.56 |
| 24 | monochloroacetaldehyde | 0.22 |
| | HF | 1.55 |
| | $O_2$ | 0.66 |

Analyses of the acidic components in the effluent show the expected conversions for HF and $Cl_2$ and a significant extent of Deacon reaction. The analyses demonstrate that oxychlorofluorination reactions take place.

EXAMPLES 25–32

These examples represent the comparative results of oxychlorofluorination reactions on acetic acid, acetyl chloride, acetic anhydride and acetaldehyde with a catalyst composition attempted to be prepared according to British Patent 745,818 (Examples 25–28) versus a typical catalyst composition according to this invention (Examples 29–32).

The parameters for the oxychlorofluorination reactions are as follows:
 Charge (Vol.) of Catalyst; 110 ml (10/20 mesh)
 Reaction Temperature; 440°
 Contact Time (seconds); 3

Preparation of Catalyst of British Patent 745,818

A sample of $Al_2(SiF_6)_3$ was mixed with 9% NaCl and pellets of about ¼ inch diameter were formed. The pellets were then heated to 950° to drive off $SiF_4$ gas.

It was attempted to impregnate the resulting $AlF_3$ pellets with 31% $CuCl_2$ loading as prescribed in the British patent. This corresponds to 45.7% Al, 38.6% Cu and 15.7% Na or a Deacon cation concentration of 45.8%. It was only possible to achieve a 23% $CuCl_2$ loading corresponding to 52.2% Al, 30.0% Cu and 17.8% Na and a Deacon catalyst cation concentration of 36.4%.

Preparation of the Comparison Catalyst

The comparison catalyst was prepared by the high temperature fluorination of a commercial alumina (Harshaw Al-0104) followed by impregnation with $CuCl_2/KCl$ as described in EXAMPLE 2 herein.

The reactions with both catalysts are performed in an alumina lined one inch tubular reactor. Catalyst bed height is 14 inches. Oxychlorofluorination takes place with both catalysts. During the reaction with the British patent catalyst, there is considerable run-off of the $CuCl_2$. This decreases the $CuCl_2$ content to 14.1% corresponding to 60.6% Al, 18.8% Cu and 20.6% Na and a Deacon catalyst cation concentration of 23.6%. The run-off of $CuCl_2$ causes considerable operating problems due to plugging, undue vaporization, excessive corrosion and lower activity due to deactivation of the fluorination sites on the carrier. Furthermore, the British patent catalyst is not fluidizable. With the comparison catalyst according to the present invention, there is no run-off of $CuCl_2$ and accordingly no accompanying operating problems due to plugging, undue vaporization, corrosion, or low activity. Furthermore, the comparison catalyst is fluidizable.

EXAMPLES 33–40

These examples demonstrate the oxychlorofluorination of the starting materials of Examples 3–10 according to this invention with a fluidized catalyst bed. The reactor is a ceramic lined pipe, 4 inches in diameter and 20 feet long. A sintered Inconel perforated disc at the bottom of the reactor serves to support the fluid bed and distribute the incoming gaseous reactants.

The catalyst used in these examples is a commercial powdered $AlF_3$ which is impregnated with $CuCl_2/KCl$ to give a composition of 91.3% Al, 5.7% Cu and 3.0% K (Deacon catalyst cation concentration - 5.8%). A sieve analysis of the coated catalyst shows the mean particle size to be 81.8 microns.

The oxychlorofluorination reactions in these examples are conducted under the following conditions:

Catalyst Charge (liters); 12
Bed Height (ft); 8
Temperature (° C); 460
Pressure (psig.); 20
Contact Time (seconds); 8.5
Gas Velocity (ft/sec); 0.95

| Feed (m/h) | |
|---|---|
| HF | 24.5 |
| HCl | 24.5 |
| $O_2$ | 24.5 |
| Starting material | 49.0 |
| $N_2$ | 0 |

Analysis of the effluents from these Examples for organic and acidic components shows essentially the same results as described in Examples 3–10.

EXAMPLES 41–48

A 180 ml. sample (3/16 inch pellets) of a $AlF_3$ catalyst which consisted of a mixture of 40% of the alpha form and 60% of the gamma form was coated with $CuCl_2/KCl$ to give a metal composition which was 97.7% Al, 1.5% Cu and 0.8% K (Deacon catalyst cation concentration -1.5%). The catalyst is charged to a 1 inch × 20 inch Inconel tubular reactor and oxychlorofluorination reactions are conducted as generally described in Examples 3–10 with the starting materials described therein. Gaseous mixtures of starting material/HCl/HF/$O_2$ having mole ratios of 2.0/1.0/1.0/1/0 are passed through a bed of the catalyst at 434°. The contact time is 4.9 seconds.

The reactions in these examples are conducted under the following conditions:

| Reactant Feed (m/h) | |
|---|---|
| HF | 0.524 |
| HCl | .427 |
| $O_2$ | .498 |

Analysis of the effluents for organic and acidic components shows essentially the same results as described in Examples 3–10.

EXAMPLES 49–56

A 20 ml. sample (10–20 mesh size) of alpha $AlF_3$ was coated with $CuCl_2/KCl$ to give a metal composition of 87.7% Al, 7.7% Cu and 4.6% K (Deacon catalyst cation concentration - 8.7%). This composition is charged to a 1 inch × 20 inch tubular Inconel reactor and oxychlorofluorination reactions are performed as generally described in Examples 3–10 on the starting materials of Examples 3–10. Gaseous mixtures of starting material/HCl/HF/$O_2$ having mole ratios of 2.0/1.0/1.0/1.0 are passed through a bed of the catalyst at 419°. The contact time is 1.7 seconds.

The reactions in these Examples are conducted under the following conditions:

| Reactant Feed (m/h) | |
|---|---|
| HF | 0.175 |
| $O_2$ | .159 |
| $Cl_2$ | .09 |

Analysis of the effluents for organic and acidic components shows essentially the same results as described in Examples 3–10.

EXAMPLES 57–83

Oxychlorofluorination reactions are conducted as described in Example 3, except with conditions starting materials and catalyst compositions changed as described in the following Table:

TABLE IV

| Example | Starting Material | Deacon Catalyst | Support | Promoter | Temperature | Pressure | Deacon Catalyst | Contact Time (seconds) |
|---|---|---|---|---|---|---|---|---|
| 57 | n-butyric acid | $Cu_2O$ | $MgF_2$ | LiCl | 425 | 14.7 | 4 | 9 |
| 58 | isobutyric acid | $FeCl_2$ | $CaF_2$ | NaCl | 300 | 14.7 | 0.6 | 20 |
| 59 | 2-methylpropanoic acid | $Cr_2O_3$ | $BaF_2$ | RbCl | 600 | 200 | 20 | .1 |
| 60 | caproic acid | $MnBr_2$ | $V_2O_3$ | $LaCl_3$ | 550 | 20 | 1 | 18 |
| 61 | capric acid | $SnCl_2$ | $ThF_4$ | $TaCl_5$ | 350 | 75 | 16 | 2 |
| 62 | n-palmityl bromide | $NiBr_2$ | $SrF_2$ | KCl | 500 | 50 | 2 | 6 |
| 63 | cyclohexane carboxylic acid | $RhCl_3$ | $CoF_2$ | $TaCl_5$ | 500 | 40 | 8 | 3 |
| 64 | n-lauraldehyde | $VCl_3$ | $NiF_2$ | CsCl | 375 | 30 | 7.5 | 6 |
| 65 | n-myristic anhydride | $CoO_2$ | $CdF_2$ | — | 450 | 25 | 19 | 12 |
| 66 | dimethylacetaldehyde | $PdCl_2$ | PbO | — | 475 | 14.7 | 0.8 | 18 |
| 67 | cyclohexanal | $Cd(NO_3)_2$ | $CrF_3$ | — | 325 | 14.7 | 1.5 | 15 |
| 68 | isobutyryl chloride | $HgBr_2$ | $Fe_2O_3$ | — | 625 | 225 | 2.5 | 10 |
| 69 | acetic acid | $PbCl_2$ | $AlF_3$ | — | 575 | 250 | 5 | 4 |
| 70 | acetyl fluoride | $Ce(NO_3)_3$ | $AlF_3$ | — | 550 | 350 | 1.12 | 5 |
| 71 | caproyl bromide | $Cr_2O_3$ | $SrF_2$ | — | 475 | 14.7 | 0.8 | 18 |
| 72 | caproic anhydride | $RhCl_3$ | $BaF_2$ | K | 350 | 25 | 2 | 10 |
| 73 | stearic acid | $PdCl_2$ | $V_2O_3$ | $CaCl_3$ | 500 | 30 | 16 | 3 |
| 74 | n-palmityl fluoride | $FeCl_2$ | $CoF_2$ | — | 600 | 200 | 4 | 12 |
| 75 | isobutyric anhydride | $HgBr_2$ | $NiF_2$ | — | 325 | 14.7 | 1.5 | 6 |
| 76 | caproaldehyde | $Cu_2O$ | $ThF_4$ | $LaCl_3$ | 425 | 20 | 0.6 | 9 |
| 77 | dimethylacetaldehyde | $MnBr_2$ | $MgF_2$ | — | 300 | 75 | 20 | 20 |
| 78 | myristaldehyde | $SnCl_2$ | $CaF_2$ | — | 550 | 50 | 1 | .1 |
| 79 | isobutyryl iodide | $NiBr_2$ | $CdF_2$ | — | 375 | 40 | 8 | 2 |
| 80 | acetyl bromide | $VCl_3$ | PbO | KCl | 500 | 14.7 | 19 | 6 |
| 81 | isopropionyl chloride | $CoO_2$ | $CrF_3$ | — | 450 | 14.7 | 7.5 | 18 |
| 82 | n-propionic acid | $Cd(NO_3)_2$ | $Fe_2O_3$ | — | 625 | 250 | 2.5 | 15 |
| 83 | acetaldehyde | $PbCl_2$ | $AlF_3$ | CsCl | 575 | 225 | 5 | 4 |

The oxychlorofluorination reactions proceed in a satisfactory manner in all of Examples 57–83.

We claim:

1. The process for the production of chlorofluorinated carboxylic acids which comprises reacting a gaseous mixture of a starting material selected from a saturated, aliphatic, carboxy containing compound, a saturated aliphatic carboxylic acid halide and a saturated aliphatic aldehyde in which all atoms are selected from C, H and O, and corresponding hydrohalogenated compounds in which the halo atoms are selected from chloro and fluoro, or mixtures thereof, oxygen in an oxygen-containing gas, HCl or $Cl_2$ and HF, in the presence of a Deacon catalyst supported by a stable, inert metal salt carrier, with the weight percentage of cation in the Deacon catalyst ranging from about 0.6–20 based on the total cation content of the Deacon catalyst and metal salt carrier, at elevated temperatures and with a contact line of from about 0.1–20 seconds.

2. The process according to claim 1 in which the starting material is selected from carboxylic acids, carboxylic acid halides and carboxylic acid anhydrides.

3. The process according to claim 1 in which the catalyst bed is maintained as a fixed bed and in which the contact time is from about 1–18 seconds.

4. The process according to claim 3 in which the contact time is from about 2–6 seconds.

5. The process according to claim 1 in which the catalyst bed is maintained as a dynamic bed.

6. The process according to claim 5 in which the catalyst bed is maintained as a fluidized bed and in which the contact time is from about 3–20 seconds.

7. The process according to claim 6 in which the contact time is from about 6–12 seconds.

8. The process according to claim 1 in which at least 0.10 mole oxygen in an oxygen-containing gas per C—H bond in the starting material is employed.

9. The process according to claim 1 in which at least 0.10 mole HCl or equivalent of $Cl_2$ for each C—H bond present in the starting material is employed.

10. The process according to claim 1 in which at least 0.25 mole oxygen-containing gas and at least 0.25 mole HCl or equivalent of $Cl_2$ for each C—H bond present in the starting material are employed.

11. The process according to claim 1 in which at least 0.50 mole oxygen in an oxygen containing gas and at least 0.50 mole HCl or equivalent of $Cl_2$ for each C—H bond present in the starting material are employed.

12. The process according to claim 1 in which the Deacon catalyst is a metal halide.

13. The process according to claim 12 in which the Deacon catalyst is promoted with a metal salt in which the metal is selected from the group consisting of Li, Na, K, Rb, La and Cs.

14. The process according to claim 1 in which the Deacon catalyst is a copper halide.

15. The process according to claim 1 in which the Deacon catalyst is $CuCl_2$.

16. The process according to claim 1 in which the carrier is a metal salt in which the metal is selected from the group consisting of Al, Mg, Ca, Ba, V, Th, Sr, Co, Ni, Cd, Pb, Cr and Fe, or combinations thereof.

17. The process according to claim 16 in which the anion of the salt is a fluoride.

18. The process according to claim 17 in which the metal salt is $AlF_3$.

19. The process according to claim 18 in which the $AlF_3$ is substantially in alpha form.

20. The process according to claim 1 in which the starting material contains up to 18 carbon atoms.

21. The process according to claim 20 in which the starting material is a carboxylic acid.

22. The process according to claim 21 in which the starting material is acetic acid.

23. The process according to claim 20 in which the starting material is a carboxylic acid halide.

24. The process according to claim 20 in which the starting material is a carboxylic acid anhydride.

25. The process according to claim 24 in which the starting material is acetic anhydride.

26. The process according to claim 20 in which the starting material is an aldehyde.

27. The process according to claim 26 in which the starting material is acetaldehyde.

28. The process according to claim 20 in which the starting material is a corresponding hydrohalogenated compound.

29. The process according to claim 28 in which the starting material is monochloroacetyl chloride.

30. The process according to claim 1 in which at least 0.75 mole oxygen in an oxygen-containing gas per C—H bond in the starting material is employed.

31. The process according to claim 30 in which at least 0.25 mole HCl or equivalent of $Cl_2$ for each C—H bond present in the starting material is employed.

32. The process according to claim 31 in which the contact time is from about 2–12 seconds.

33. The process according to claim 31 in which the gaseous mixture of starting material is diluted with an inert gas.

34. The process according to claim 31 in which the starting marterial is a saturated aliphatic aldehyde.

35. The process according to claim 31 in which the weight percentage of cation in the Deacon catalyst ranges from about 1–16 based on the total cation content of the Deacon catalyst and metal salt carrier.

36. The process according to claim 31 in which the elevated temperatures range from about 300°–600° C.

37. The process according to claim 35 in which the Deacon catalyst is a metal halide.

38. The process according to claim 37 in which the Deacon catalyst is promoted with a metal salt in which the metal is selected from the group consisting of Li, Na, K, Rb, La and Cs.

39. The process according to claim 35 in which the Deacon catalyst is a copper halide.

40. The process according to claim 35 in which the Deacon catalyst is $CuCl_2$.

41. The process according to claim 35 in which the carrier is a metal salt in which the metal is selected from the group consisting of Al, Mg, Ca, Ba, V, Th, Sr, Co, Ni, Cd, Pb, Cr and Fe.

42. The process according to claim 41 in which the anion of the salt is a fluoride.

43. The process according to claim 42 in which the metal salt is $AlF_3$.

44. The process according to claim 35 in which the reaction gas mixture is diluted with an inert gas.

45. The process according to claim 35 in which the weight percent of cation in the Deacon catalyst ranges from about 2–8 based on the total cation content of the Deacon catalyst and metal salt.

46. The process according to claim 35 in which the Deacon catalyst is a metal halide and in which the carrier is a metal salt in which the metal is selected from the group consisting of Al, Mg, Ca, Ba, Th, Sr, Co, Ni, Cd, Pb, Cr and Fe.

47. The process according to claim 46 in which the Deacon catalyst is $CuCl_2$.

48. The process according to claim 47 in which the metal salt carrier is $AlF_3$.

49. The process according to claim 46 in which the anion of the metal salt carrier is a fluoride.

50. The process according to claim 49 in which the metal salt is $AlF_3$.

51. The process according to claim 50 in which the $AlF_3$ is substantially in the alpha form.

52. The process for the production of chlorofluorinated carboxylic acids which comprises reacting a gaseous mixture of a starting material selected from saturated, aliphatic carboxy containing compounds, a saturated aliphatic carboxylic acid halide and a saturated aliphatic aldehyde in which all atoms are selected from C, H and O, and corresponding hydrohalogenated compounds in which the halo atoms are selected from chloro and fluoro, or mixtures thereof, at least .25 mole oxygen in an oxygen-containing gas for each C—H bond in the starting material, at least 2 mole HCl or equivalent $Cl_2$ per mole of starting material, and HF, in the presence of a Deacon catalyst supported by a stable, inert metal salt carrier, with the weight percentage of cation in the Deacon catalyst ranging from about 0.6–20 based on the total cation content of the Deacon catalyst and metal salt carrier, at elevated temperatures and with a contact time of from about 0.1–20 seconds.

* * * * *

UNITED STATES PATENT AND TRADEMARK OFFICE
CERTIFICATE OF CORRECTION

PATENT NO. : 4,105,691

DATED : August 8, 1978

INVENTOR(S) : Richard F. Sweeney, James O. Peterson, Bernard Sukornick, Henry R. Nychka, Richard E. Eibeck and Morris B. Berenbaum It is certified that error appears in the above-identified patent and that said Letters Patent are hereby corrected as shown below:

Column 5, line 1, "adre" should be -- are --.

Column 5, line 12, "inhert" should be -- inert --.

Column 17, claim 1, line 45, "line" should be -- time --.

Signed and Sealed this

Seventh Day of August 1979

[SEAL]

Attest:

LUTRELLE F. PARKER

Attesting Officer

Acting Commissioner of Patents and Trademarks